(12) United States Patent
McDonnell et al.

(10) Patent No.: US 7,112,685 B2
(45) Date of Patent: Sep. 26, 2006

(54) LABELED RESINIFERATOXIN DERIVATIVES

(75) Inventors: Mark E. McDonnell, Lansdale, PA (US); Larry E. Weaner, Palmyra, NJ (US); Sui Po Zhang, Bala Cynwyd, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 112 days.

(21) Appl. No.: 09/973,378

(22) Filed: Oct. 9, 2001

(65) Prior Publication Data

US 2004/0230064 A1 Nov. 18, 2004

Related U.S. Application Data

(60) Provisional application No. 60/239,627, filed on Oct. 10, 2000.

(51) Int. Cl.
*C07D 321/10* (2006.01)
*C07D 321/12* (2006.01)

(52) U.S. Cl. ........................ 549/348; 549/349
(58) Field of Classification Search ........... 549/348, 549/349; 514/450
See application file for complete search history.

(56) References Cited

U.S. PATENT DOCUMENTS 5,232,684 A 8/1993 Blumberg et al.

FOREIGN PATENT DOCUMENTS

WO  WO 98/20867 A1  5/1998
WO  WO 9/09140 A1  2/1999

OTHER PUBLICATIONS

S. Bevan and J. Szolcsanyi, Sensory neuron–specific actions of capsaicin: mechanisms and applications, Trends Pharmacol Sci, Aug. 1990 vol. 11 pp. 330–333.
J. Szolcsanyi, Capsaicin–sensitive sensory nerve terminals with local and systemic efferent functions: facts and scopes of an unorthodox neuroregulatory mechanism, Progress in Brain Research, 1996, vol. 113, pp. 343–359.
Szolcsanyi et al., Resiniferatoxin: An Ultrapotent Neurotoxin of Capsaicin–sensitive Primary Afferent Neurons, Annals of the New York Academy of Sciences, 1991 vol. 632, pp. 473–475.
Veronesi et al., Particulate Matter initiates Inflammatory Cytokine Release by Activation of Capsaicin and Acis Receptors in a Human Bronchial Epithlial Cell Line, Toxicology and Applied Pharmacology 154, (1999) pp. 106–115.
Winter J et al, Capsaicin and pain mechanisms, British Journal of Anaesthesia 1995: 75: 157–168.
Caterina MJ, et al., The capsaicin receptor: a heat–activated ion channel in the pain pathway, Nature, vol. 389 Oct. 1997, pp. 816–824.
Tominaga M et al., The Cloned Capsaicin Receptor Integrates Multiple Pain–Producing Stimuli, Neuron, vol. 21, pp. 531–543 Sep. 1998.
Wood JN et al., Capsaicin–Induced Ion Fluxes in Dorsal Root Ganglion Cells in Culture, The Journal of Neuroscience, Sep. 1988, 8(9): 3208–3220.
Bevan S. et al., Capsazepine: a competitive antagonist of the sensory neurone excitant capsaicin, Br. J Pharmacol, (1992), 107, pp. 544–552.
Harvey, JS et al., Activation of Protein Kinase C by the Capsaicin Analogue Resiniferatoxin in Sensory Neurones, Journal of Neurochemistry 65: 1995 1309–1317.
Szallasi, Goso et al, Competitive Inhibition by Capsazepine of [$^3$H]Resiniferatoxin Binding to Central (Spinal Cord and Dorsal Root Ganglia) and Peripheral (Urinary Bladder and Airways) Vanilloid (Capsaicin) Receptors in the Rat, J Pharmacol Exp Ther, 267: 728–33 1993.
Szallasi & Goso, Characterization by [$^3$H]resiniferatoxin binding of a human vanilloid (capsaicin) receptor in post–mortem spinal cord, Neuroscience Letters, 165(1994) 101–104.
Szallasi A & Blumber PM, Specific binding of resiniferatoxin, an ultrapotent capsaicin analog, by dorsal root ganglion membranes, Brain Research, 524, (1990) 106–111.
ACS, M Palkovits, Blumberg, [3H]Resiniferatoxin binding by the human vanilloid (capsaicin) receptor, Molecular Brain Research, 23: 185–90, 1994.
Blumberg et al., Labelled Resiniferatoxin, Compositions Thereof, and Methods for Using the Same., Filed Jun. 29, 1990, National Institute of Health, Bethesda, MD, Report Nos: PAT–APPL–7–546 141 48pages.
Andil et al., "A practical and Cost–Effective Synthesis of 6,7–Dimethoxy–2–tetralone", SYNTHESIS, vol. 12, 1999, pp. 2033–2035, XP002208174.
Walpole et al., "Similarities and Differences in the SAR's of Capsaicin and Resininferatoxin Analogues", J.Med.Chem., vol. 39, 1996, pp. 2939–2952, XP002208173, Xcheme 4, 5$^{th}$ transformation (coupling with DCCI and DMAP).

*Primary Examiner*—Ba K. Trinh (57) ABSTRACT

This invention relates resiniferatoxin derivatives useful in a vanilloid receptor binding assay and methods for production thereof.

3 Claims, 1 Drawing Sheet

Figure 1

LABELED RESINIFERATOXIN DERIVATIVES

CROSS-REFERENCE TO RELATED APPLICATION

This application claims the benefit of provisional application Ser. No. 60/239,627, filed Oct. 10, 2000.

FIELD OF THE INVENTION

This invention relates to a method for preparing iodinated or labeled vanilloid receptor ligands. More particularly, this invention relates to a method for preparing an iodinated or labeled resiniferatoxin derivative and congeners thereof and a method for use in a vanilloid receptor binding assay.

BACKGROUND OF THE INVENTION

Noxious chemical, thermal and mechanical stimuli excite peripheral nerve endings of small diameter sensory neurons (nociceptors) in sensory ganglia (e. g., dorsal root, nodose and trigeminal ganglia) and initate signals that are perceived as pain. These neurons are crucial for the detection of harmful or potentially harmful stimuli (heat) and tissue damage ($H^+$ (local tissue acidosis), and/or stretch) which arise from changes in the extracellular space during inflammatory or ischaemic conditions (Wall, P. D., and Melzack, R., *Textbook of Pain,* 1994, New York: Churchill Livingstone).

Capsaicin, (N-[(4-hydroxy-3-methoxyphenyl)methyl]-8-methyl-6-nonenamide), the main pungent Ingredient in "hot" capsicum peppers, interacts with specific membrane recognition sites called vanilloid receptors (VR). These proteins are expressed almost exclusively by primary sensory neurons involved in nociception and neurogenic inflammation (Bevan, S., and Szolcsanyi, J., Sensory neuron-specific actions of capsaicin: mechanisms and applications, *Trends Pharmacol. Sci.,* 1990, 11, 330–3). Capsaicin itself is a selective activator of thinly myelinated or unmyelinated nociceptive afferents (Szolcsanyi, J., Actions of capsaicin on sensory receptors, In Capsaicin Study, Pain, J. N. Wood, ed.: Academic, London, UK, 1993, pp. 1–26; and Szolcsanyi, J., Capsaicin-sensitive sensory nerve terminals with local and systemic efferent functions: facts and scopes of an unorthodox neuroregulatory mechanism, *Prog. Brain Res.,* 1996, 113, 343–359).

Capsaicin and structurally-related derivatives show structure-function relationships and these effects can be blocked by a selective antagonist, capsazepine. The tricyclic diterpene resiniferatoxin (RTX) (Szolcsanyi, J., Szallasi, A., Szallasi, Z., Joo, F., and Blumberg, P. M., Resiniferatoxin: An ultrapotent neurotoxin of capsaicin-sensitive primary afferent neurons. *Ann. N. Y. Acad. Sci.,* 1991, 632, 473–5) binds at the capsaicin binding site and has revealed a very localized distribution of capsaicin receptors at rat somatic and visceral primary sensory neurons (Szallasi, A., Nilsson, S., Farkas-Szallasi, T., Blumberg, P. M., Hoekfelt, T., and Lundberg, J. M., Vanilloid (capsaicin) receptors in the rat: distribution in the brain, regional differences in the spinal cord, axonal transport to the periphery, and depletion by systemic vanilloid treatment. *Brain Res.,* 1995, 703, 175–83). Interestingly, the density of RTX receptor sites in nodose and dorsal root ganglia increased after ligation of the vagal and sciatic nerves (Szallasi et al., 1995).

Multiple effects of capsaicin on sensor neurons have been characterized (Szallasi, A. and Blumberg, P. M., Vanilloid receptor: new insights enhance potential as a therapeutic target, *Pain,* 1996, 68,195–208). Capsaicin excites the neuron resulting in calcium influx, the release of various neuropeptides such as CGRP and SP (Purkiss, J., Welch, M., Doward, S. and Foster, K, Capsaicin-stimulated release of substance P from culture dorsal root ganglion neurons: involvement of two distinct mechanisms, *Biochem. Pharmacol.,* 2000, 59, 1403–1406) and cytokine release (Veronesi, B., Oortgiesen, M., Carter, J. D. and Devlin, R. B., Particulate matter initiates inflammatory cytokine release by activation of capsaicin and acid receptors in a human bronchial epithelial cell line, *Toxicol. Appl. Pharmacol.,* 1999, 154,106–115). These events are believed to contribute to pain states and inflammation. Additionally, capsaicin and RTX can cause vanilloid receptor desensitization (Acs, G., Biro, T., Ace, P., Modarres, S. and Blumberg, P. M., Differential activation and desensitization of sensory neurons by resiniferatoxin, *J. Neurosci.,* 1997, 17, 6522–5628) which, in animals, manifests as a state of reduced nociception. This phenomenon may constitute a novel approach to the treatment of neuropathic pain (Winter, J., Bevan, S. and Campbell, E. A., Capsaicin and pain mechanism, *Br. J. Anaesth.,* 1995, 75, 157–168) and other pain states. However, under certain conditions, capsaicin and RTX can be neurotoxic (Bevan and Szolcsanyi, 1990).

Recently, one receptor protein for capsaicin was cloned from rat (Caterina, M. J., Schumacher, M. A., Tominaga, M., Rosen, T. A., Levine, J. D., and Julius, D., The capsaicin receptor: a heat-activated ion channel in the pain pathway, Nature (London), 1997, 389, 816–824) and shown to be a coincidence detector for $H^+$ (low pH) and heat (Tominaga, M., Caterina, M. J., Malmberg, A. B., Rosen, T. A., Gilbert, H., Skinner, K., Raumann, B., Basbaum, A. I., and Julius, D., The cloned capsaicin receptor integrates multiple pain-producing stimuli, *Neuron,* 1998, 21, 531–543). VRI is a ligand-gated non-selective cation channel that shows pronounced outward rectification (Caterina et al., 1997). The vanilloid ("capsaicin") receptor VR1 is activated by capsaicin and RTX, and activation of VRI is blocked by the antagonists capsazepine (CPZ) (Bevan, S., Hothi, S., Hughes, G., James, I. F., Rang, H. P., Shah, K., Walpole, C. S. J., and Yeats, J. C., Capsazepine: a competitive antagonist of the sensory neuron excitant capsaicin, *Br. J. Pharmacol.,* 1992, 107, 544–52) and ruthenium red (RR) (Wood, J. N., Winter, J., James, I. F., Rang, H. P., Yeats, J., and Bevan, S., Capsaicin-induced ion fluxes in dorsal root ganglion cells in culture, *J. Neurosci.,* 1988, 8, 3208–20). VR1 Receptors are sensitive to vanilloids, heat and protons and thus these proteins are believed to be widely involved in the initiation, modulation and modification of pain (Woolf, C. J. and Salter, M. W., Neuronal plasticity: increasing the gain in pain, *Science,* 2000, 288, 1765–11768). Furthermore, VR1 is expressed in small nociceptive neurons of the dorsal root ganglion, consistent with its role in modulating peripheral pain (Tominaga, et al., 1998; and, Michael, G. J. and Priestley, J. V., Differential expression of the mRNA for the vanilloid receptor subtype 1 in calls of the adult rat dorsal root and nodose ganglia and its downreglulation by axotomy, *J. Neurosci.,* 1999, 19, 1844–1854).

Patent application WO 99/09140 identifies the vanilloid receptor (VR) as a ligand-gated, non-selective cation channel that is expressed in sensory neurons and which is involved in nociceptive processes such as hyperalgesia. Resiniferatoxin, a naturally-occurring terpenoid phorbol derivative, binds to the VR protein with sub-nanomolar affinity and behaves as a functional agonist (stimulates calcium influx). Accordingly, iodinated and labeled RTX derivatives may similarly be potent in binding to the vanilloid receptor and may therefore be useful in identifying compounds that have affinity for vanilloid receptor when utilized in a receptor-binding assay. Indeed, tritiated-RTX is known to display a nanomolar affinity for VR, and can be used to identify or indicate compounds that also bind to this receptor.

Several [$^3$H] RTX-based VR binding assays have been disclosed: a filtration assay (Szallasi, A. and Blumberg, P. M., Specific binding of resiniferatoxin, an ultrapotent capsaicin analog, by dorsal root ganglia membranes, *Brain Res.*, 1990, 524, 106–111; and, Harvey, J. S., Davis, C., James, I. F. and Burgess, G. M., Activation of protein kinase C by the capsaicin analogue resiniferatoxin in sensory neurons, *J. Neurochem.*, 1995, 65, 1309–1317) and a centrifugation assay (Szallasi, A., Goso, C., Blumberg, P. M., and Manzini, S., Competitive inhibition by capsazepine of [$^3$H] resiniferatoxin binding to central (spinal cord and dorsal root ganglia) and peripheral (urinary bladder and airways) vanilloid (capsaicin) receptors in the rat, *J. Pharmacol. Exp. Ther.*, 1993, 267, 728–33; Szallasi, A. and Goso, C., Characterization by [$^3$H] resiniferatoxin binding of a human vanilloid (capsaicin) receptor in post-morten spinal cord, *Neurosci. Letters*, 1994, 165, 101–104; and, Acs, G., Palkovits, M., and Blumberg, P. M., [$^3$H] Resiniferatoxin binding by the human vanilloid (capsaicin) receptor, *Mol. Brain Res.*, 1994, 23, 185–90). Use of filtration assay protocols is hampered by a high non-specific binding. Using the centrifugation assay, VRI receptors were found in several tissues, such as, dorsal root ganglia, spinal cord, dorsal vagal complex, trachea and main bronchi and urinary bladder. The affinities of [$^3$H]RTX to the VR1 receptor were different with different tissues (Szallasi, A. and Blumberg, P. M., Vanilloid (capsaicin) receptors and mechanisms, *Pharmacol. Rev.*, 1999, 51, 159–211). High expression of VR1 receptors was observed in human and rat spinal cord and dorsal root ganglia tissues (Szallasi, et al, 1993; Szallasi and Goso, 1994; and, Acs, et al., 1994). The affinity of [$^3$H]RTX to VR1 receptors in rat spinal cord is higher than that in human spinal cord (Szallasi and Goso, 1994).

U.S. patent application 546,141 A0 to Blumberg, et. al., filed Apr. 15, 1991, describes labeled RTX or labeled congeners thereof, wherein representative radiolabels include tritium, $^{125}$iodine [$^{125}$I] and $^{131}$iodine [$^{311}$] having a preferred formula:

Other representative congeners of RTX include those of the formula:

wherein n is 0 to 10 n is 0 to 10, preferably 2, and R' is a fluorescent label. In lieu of radiolabeled RTX, the Blumberg application describes that biologically active congeners of RTX can be radiolabeled using the same synthetic route as for tritiated RTX, wherein such congeners have the general structure:

wherein R is:

$R_3$ is OH, x is 0 or 1, $R_1$, $R_2$, $R_4$ and $R_5$ each are: H, OH, OC(=O)(CH$_2$)$_n$H, O(CH$_2$)$_n$H with n=0 to 10. In labeled compounds of the above congeners, at least of $R_1$, $R_2$, $R_4$ or $R_5$ is labeled, for instance, with $^3$H, $^{125}$I or $^{131}$I. In this formula, one of more of $R_1$, $R_2$, $R_4$, and $R_5$ is $^3$H. $R_3$ should be OH so that the derivative is active. The preparation of 125I or 131I labeled RTX, tinyatoxin and congeners thereof possessing an unsubstituted m-hydrogen on the substituted phenylacetic acid side chain have been described, wherein such compounds can be prepared by iodination using chloramine T or using glucose oxidase or lactoperoxidase and, in the described compounds, one or more of $R_1$, $R_2$, $R_4$ and $R_5$ may be $^{125}$I or $^{131}$I.

PCT patent application WO 98/20867 to Blumberg, et. al., describes a pharmaceutical composition comprising a capsaicin agonist, a capsaicin antagonist and a pharmaceutically acceptable carrier wherein the capsaicin agonist is of the formula:

wherein $R_1$ is:

$R_2$ is hydroxy or methoxy; $R_3$ is loweralkylaryl or an aryl group having 1 to 3 rings; and, $R_4$ to $R_7$, which may be the same or different, are independently selected from the group consisting of hydrogen, hydroxy, methoxy, sulfhydryl, nitro, amino, ethoxy, halo and $OCOCH_3$.

No reference has heretofore disclosed a method for preparing an iodinated or labeled resiniferatoxin derivative. The object of the present invention is to provide a method for preparing an iodinated resiniferatoxin derivative and congeners thereof. Another object of the invention is to provide a method for preparing a labeled resiniferatoxin derivative and congeners thereof. Also another object of the invention is to provide a method for iodinating or labelling a specific site of a para-O-acetylated vanilloid receptor intermediate. A further object of the invention is to provide a method for use of an Iodinated or labeled resiniferatoxin derivative and congeners thereof in a vanilloid receptor binding assay.

SUMMARY OF THE INVENTION

The present invention provides a method for preparing a resiniferatoxin derivative compound of Formula (I):

Formula (I)

wherein
$R^1$ is a substituent selected from the group consisting of hydrogen, $C_{1-4}$alkylcarbonyl and formyl;
$R^2$ is iodine; and,
$R^3$ is a substituent selected from the group consisting of $C_{1-4}$alkoxy and hydroxy; comprising, iodinating the ortho position on the phenyl ring of a homovanillic acid derivative compound of Formula (II);

Formula (II)

to form an intermediate compound of Formula (III); and,

Formula (III)

coupling the intermediate compound of Formula (III) with a resiniferonal orthophenylacetate alcohol compound of Formula (IV);

Formula (IV)

to form the compound of Formula (I).

A preferred embodiment of the method of the present invention includes a resiniferatoxin derivative compound wherein $R^1$ is acetyl; and, $R^3$ is methoxy. A more preferred embodiment includes a resiniferatoxin derivative compound wherein $R^2$ is $^{127}$iodine. The most preferred embodiment includes a labeled resiniferatoxin derivative compound wherein $R^2$ is selected from the group consisting of $^{125}$iodine and $^{131}$iodine.

Relative to the foregoing description of a method for producing a labeled resiniferatoxin derivative of the present invention, another embodiment of the invention is a method for preparing a labeled resiniferatoxin derivative compound of Formula (V):

Formula (V)

wherein
$R^1$ is a substituent selected from the group consisting of hydrogen, $C_{1-4}$alkylcarbonyl and formyl; and,
$R^3$ is $C_{1-4}$alkoxy; comprising, protecting the carboxylic acid of an intermediate compound of Formula (VI);

Formula (VI)

wherein the hydroxyl group of the compound of Formula (VI) is esterified with $C_{1-5}$ alkyl to form an esterified intermediate compound of Formula (VII);

Formula (VII)

stannylating the compound of Formula (VII) to form a stannylated intermediate compound of Formula (VIII);

Formula (VIII)

iodinating the compound of Formula (VIII) to form a labeled intermediate compound of Formula (IX);

Formula (IX)

deprotecting the compound of Formula (IX) to form a labeled intermediate compound of Formula (X); and, Formula (X)

coupling the labeled intermediate compound of Formula (X) with a resiniferonal orthophenylacetate alcohol compound of Formula (IV);

Formula (IV)

to form the compound of Formula (V).

In a preferred embodiment, $C_{1-5}$alkyl is selected from the group consisting of i-propyl, i-butyl and t-butyl. In a more preferred embodiment, $C_{1-5}$alkyl is t-butyl.

The present invention also provides a resiniferatoxin derivative compound of Formula (I) for use in a vanilloid receptor binding assay:

Formula (I)

wherein
$R^1$ is a substituent selected from the group consisting of hydrogen, $C_{1-4}$alkylcarbonyl and formyl;
$R^2$ is iodine; and,
$R^3$ is a substituent selected from the group consisting of C1-4alkoxy and hydroxy.

DETAILED DESCRIPTION OF THE INVENTION

Figure 1:
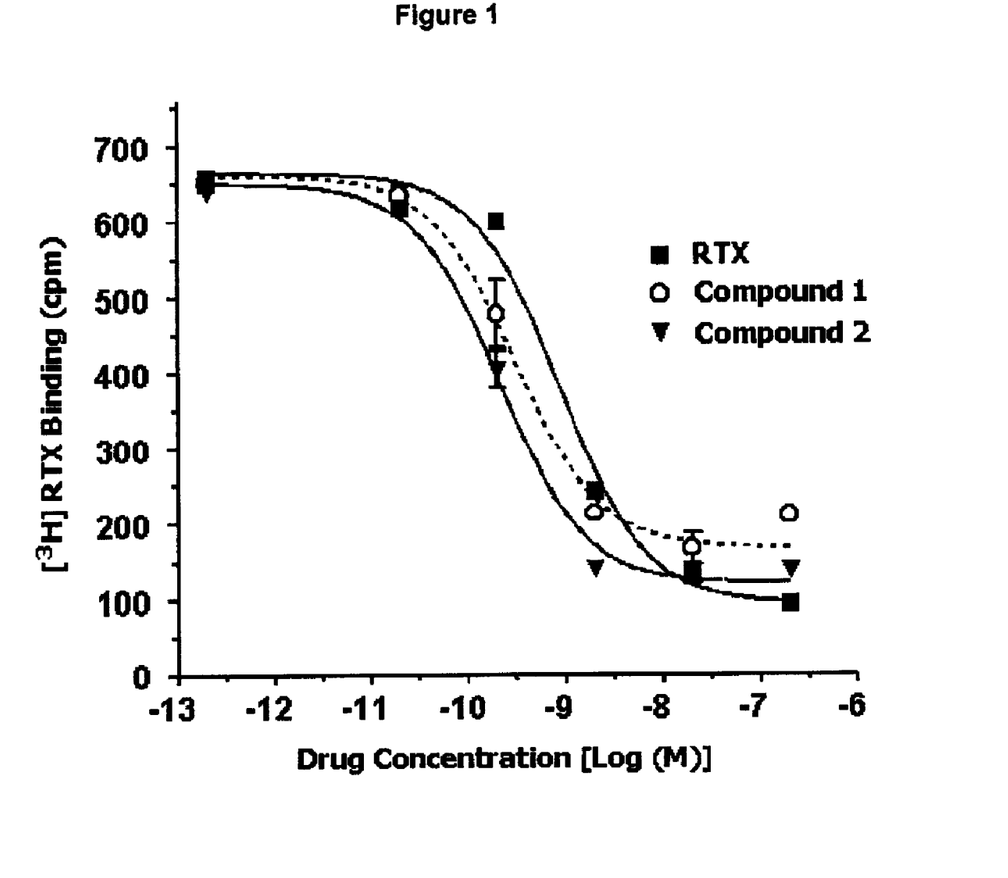
FIG. 1 shows the inhibition of [$^3$H] RTX binding to hVR1 receptors in counts per minute (cpm) as a function of the $IC_{50}$ drug concentration value in Log Mole (M) of an iodinated RTX derivative.

The current reference standard for identifying compounds that bind to the resiniferatoxin receptor is labeling such RTX compounds with tritium [$^3$H]. The use of a [$^3$H] labeled RTX compound is limited, however, by such compounds having different affinities for different tissues and high non-specific binding. Furthermore, current methods for preparing an iodinated or labeled resiniferonal-vanilloid derivative RTX compound have been limited by undirected iodination on the aromatic ring of the vanilloid substrate, thus resulting in iodination or labeling on different and multiple positions. The undirected iodination or labeling of the present art results in inseparable mixtures of iodinated compounds, batch to batch variations, significantly poorer binding affinity than a [$^3$H] labeled derivative and non-reproducible, non-productive assay data.

As used herein, the term "iodine" is intended to include both the nonradioactive and radioactive isotopes of iodine.

Preferred iodine isotopes are those commonly used in chemical reactions. Such commonly used isotopes include the nonradioactive isotope $^{127}$iodine [$^{127}$I] and radioactive isotopes $^{125}$iodine and $^{131}$iodine.

Alternatively, we have recently discovered that iodinated RTX analogs or labeled RTX analogs (in particular, those analogs labeled using $^{125}$I or $^{131}$I are intended to be included in the scope of the present invention) have the advantage of an improved binding affinity over a [$^3$H] labeled RTX derivative, thus enabling smaller amounts of receptor sites to be detected while using a lower ligand concentration to assay those receptors.

We have also discovered that the iodination reaction and consequent iodination or labeling of a RTX derivative may be consistently directed to a single position on the vanilloid substrate, thus providing a RTX compound containing a single site of iodination which is free of the limitations inherent in current methods of preparation. Moreover, the method of the present invention comprises iodinating the single vanilloid substrate site wherein a single iodine atom may be consistently incorporated. Accordingly, the present method may be used to iodinate the ortho position on the phenyl ring of a para-O-carbonylalkyl substituted homovanillic acid substrate of an RTX derivative compound. Included within the scope of the invention is the corresponding para des-carbonylalkyl substituted homovanillic acid substrate of the RTX derivative compound. A preferred embodiment of the present method for iodinating or labeling a RTX derivative compound comprises iodinating or labeling the ortho position on the phenyl ring of a homovanillic acid acetate ester derivative substrate with a single iodine atom or iodine-based label, preferably $^{125}$I; and, coupling the iodinated or labeled vanilloid derivative with a resiniferonal orthophenylacetate alcohol to form a resiniferotoxin or labeled resiniferotoxin derivative compound of the present invention.

The advantage of the method of the present invention is embodied in a "directed-iodination" in which a single iodine substituent is specifically introduced onto a single specific carbon center of a homovanillic acid substrate or intermediate compound. In the method of the present invention, the iodination is directed to the ortho position of the phenyl group in the vanilloid acid substrate by an O-acetate protecting group. We have also discovered that iodination at the ortho position is not accessible using other common protecting groups, particularly those that do not withdraw electron density from the aromatic system of the homovanillic acid.

The use of substituents for the R$^1$ group of the homovanillic acid substrate other than C$_{1-4}$alkylcarbonyl and formyl (preferably, R$^1$ is selected from acetyl and formyl; and, more preferably, R$^1$ is acetyl) did not give a very clean iodination reaction or a high degree of regiospecificity. It was determined that previously disclosed iodination reactions of homovanillic acid and homovannillic acid ethyl ester did not yield the ortho-iodinated product regioselectively as did the iodination of the 4-acetoxy-3-methoxyphenylacetic acid substrate of the present invention. The efficiency of the instant method compared to the lack of specificity resulting from the use of previously disclosed iodination reactions for the homovanillic acid substrate can be characterized using techniques known to those skilled in the art such as, but not limited to, HPLC.

Moreover, we have discovered that [$^3$H] labeled RTX analogs have binding affinities for the vanilloid receptor at generally three to four orders of magnitude less than the iodinated or labeled RTX derivatives of the present invention. Taking into account how modifications of the aryl ring affect binding (C. S. Walpole, S. Bevan, G. Bloomfield, R. Breckenridge, I. F. James, T. Ritchie, A. Szallasi, J. Winter, R. Wrigglesworth., Similarities and Differences in the Structure-Activity Relationships of Capsaicin and Resiniferatoxin Analogues, *J. Med. Chem.*, 1996, 39, 2939–2952), it was indeed surprising that the instant iodinated RTX derivatives reproducibly exhibited sub-nanomolar affinity for the vanilloid receptor and maintained a binding affinity that was similar to a [$^3$H] labeled derivative commonly used and known to those skilled in the art.

The scope of the present invention includes a method for iodinating a homovanillic acid intermediate, a method for labeling a homovanillic acid intermediate and a method for using such intermediates in a RTX binding assay. Furthermore, a compound or an intermediate iodinated or labeled by the method of this invention may be used to subsequently prepare other novel RTX compounds that carry the unique and novel site of iodination. For example, compounds in which R$^1$ is hydrogen may not be suitable for production by the methods described above. A particular step for which R$^1$ is hydrogen may not be suitable is that step wherein an iodinated or labeled homovanillic acid intermediate compound is produced. For such a step, it is preferred that R$^1$ is C$_{1-4}$alkylcarbonyl or formyl. Compounds in which R$^1$ is hydrogen that may be produced are those from analogous compounds in which R$^1$ is C$_{1-4}$alkylcarbonyl or formyl by either of two methods. In a first method, for compounds in which R$^1$ is C$_{1-4}$alkylcarbonyl or formyl, the R$^1$ group may be cleaved chemically in a separate chemical reaction using common literature methods or specifically, as disclosed herein, with pyrrolidine. In a second method, for compounds in which R$^1$ is C$_{1-4}$alkylcarbonyl or formyl that are used in a binding assay, the in situ esterase or pH conditions may cleave the R$^1$ group to hydrogen.

Relative to the above generic description for a compound of Formula (I), certain compounds of Formula (I) are preferred. Preferred embodiments are those compounds wherein R$^1$ is a substituent selected from the group consisting of hydrogen, formyl, acetyl, ethylcarbonyl and propylcarbonyl;

more preferably, R$^1$ is a substituent selected from the group consisting of hydrogen, formyl and acetyl;

most preferably, R$^1$ is a substituent selected from the group consisting of hydrogen and acetyl;

R$^2$ is a substituent selected from the group consisting of $^{125}$iodine, $^{127}$iodine and $^{131}$iodine;

more preferably, R$^2$ is a substituent selected from the group consisting of $^{125}$iodine and $^{127}$iodine;

R$^3$ is a substituent selected from C$_{1-4}$alkoxy;

more preferably, R$^3$ is a substituent selected from methoxy, ethoxy, propoxy and butoxy; and, most preferably, R$^3$ is methoxy.

Exemplified compounds of the present invention are those of the formula:

wherein $R^1$ and $R^2$ are selected from

| Cmpd | $R^1$ | $R^2$ |
|------|-------|-------|
| 1 | $C(O)CH_3$ | I; |
| 2 | H | I; |
| 3 | $C(O)CH_3$ | $^{125}$iodine, $^{131}$iodine; |
| 4 | H | $^{125}$iodine or $^{131}$iodine. |

The terms used in describing the invention are commonly used and known to those skilled In the art. Abbreviations used in the instant specification, particularly the Schemes and Examples, are as follows:

| | |
|---|---|
| DCC | Dicyclohexylcarbodiimide |
| DMAP | 4-Dimethylaminopyridine |
| $I_2$ | Iodine |
| $AgO_2CCF_3$ | Silver trifluoroacetate |
| NaI | Sodium iodide |
| $Fe_2SO_4$ | Iron sulfate |
| TFA | Trifluoroacetic acid |

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme A illustrates a method for producing an iodinated vanilloid substrate of a resiniferatoxin derivative by the use of an electron withdrawing group, whereby the homovanillic acid hydroxyl group is derivatized and the acetate ester group necessary to direct the site of iodination is formed.

Compound A1 used as the starting material was derived from homovanillic acid by derivatizing the hydroxyl moiety and forming the acetate ester group using excess acetic anhydride and a catalytic amount of sulfuric acid. Compound A1 was then treated with an in situ generated electrophilic iodine species for 24 hours at room temperature which resulted in Compound A2. The iodinated homovanillic acid Compound A2 was then coupled with a resiniferonol orthophenylacetate alcohol Compound A3 by a dimethylaminopyridine mediated catalysis and carbodiimide mediated esterification under suitable conditions after two hours to form the target Compound A4.

Scheme A

Scheme B illustrates a method for producing an iodinated vanilloid substrate of a resiniferatoxin derivative wherein $R^1$ is hydrogen by cleaving the acetyl $R^1$ substituent from Compound A4 with an amine base such as pyrrolidine to produce Compound B1. This reaction was carried out at room temperature for two hours in methylene chloride.

Scheme B

Scheme C illustrates a method for producing a labeled vanilloid substrate of a resiniferatoxin derivative by the direct labeling of homovanillic acid Compound A1 using hot sodium iodide in the presence of an oxidant to form Compound C1. This reaction is carried out in methylene chloride at room temperature for several hours.

Scheme C

C1

Scheme D illustrates a method for producing a labeled vanilloid substrate of a resiniferatoxin derivative by the stannylation of an iodinated compound of the present invention to a trimethyl tin compound and subsequent conversion of the trimethyl tin to a $^{125}$I or $^{131}$I labeled compound, incorporating methods well described in the literature and providing an alternative preparation route.

In Scheme D, the carboxylic acid moiety of a 4-acetylhomovanillic acid Compound A2 is protected by esterification with a $C_{1-5}$alkyl group such as i-propyl, i-butyl or t-butyl to form the ester Compound D1. The iodine on the 2-iodo4-acetylhomovanillic acid Compound D1 is then converted via a palladium catalyzed metallation to a trimethyl tin group and, using sodium iodide and an oxidant, is subsequently converted to the $^{125}$I or $^{131}$I labeled Compound D2. The $C_{1-5}$alkyl group from the esterified Compound D2 is selectively cleaved in the presence of the acetate ester using an acidic hydrolysis to form Compound D3. The $^{125}$I labeled homovanillic acid Compound D3 is then coupled with resiniferonol orthophenylacetate Compound A3 via the carbodiimide esterification shown in Scheme A to form Compound D4.

Scheme D

D2

+

D3

A3

-continued

D4

Specific Synthetic Methods

Specific compounds which are representative of this invention may be prepared as per the following examples offered by way of illustration and not by way of limitation. No attempt has been made to optmize the yields obtained in any of the reactions. One skilled in the art would know how to increase such yields through routine variations in reaction times, temperatures, solvents and/or reagents.

Procedure 1

2-Iodo-4-acetoxy-5-methoxyphenylacetic acid

4-Acetoxy-3-methoxyphenylacetic acid (200 mg, 0.89 mmol), silvertrifluoroacetate (217 mg, 0.98 mmol) and iodine (237 mg, 0.93 mmol) were combined and stirred in dry dichloromethane (20 mL) for 2 hours under argon. The reaction was filtered. The filtrate was washed (sat. NaCl solution), dried ($MgSO_4$), and stripped to afford the title compound as a white powder (yield=279 mg; 89%). Analytical reverse phase HPLC (gradient 10–90% MeCN, 0.1% aqueous TFA) $t_R$=3.56 min, ~99%; $^1$H NMR ($CD_3OD$, 300 MHz) δ 7.46 (s, 1H), 7.10 (s, 1H), 3.79 (s, 3H), 3.78 (s, 2H), 2.24 (s, 3H); $^{13}$C NMR ($CD_3OD$, 300 MHz) δ 174.4, 170.7, 153.3, 140.9, 138.8, 134.1, 116.5, 88.8, 56.9, 46.9, 20.7. Anal. calcd for $C_{11}H_{11}O_5I_1$: C, 37.74; H, 3.17. Found: C, 37.93; H, 3.31.

Procedure 2

2-$^{251}$Iodo-4-acetoxy-5-methoxyphenylacetic acid

Iron (III) sulfate (11.3 nmol), sodium 125iodide (6.6 nmol), water (100 microliters) and dichloromethane (150 microliters) are placed into a 1 mL v-vial with a stirrer. The mixture is vigorously stirred for 40 min at ambient temperature and the violet-colored organic layer is removed using a syringe. The solution is then added to a v-vial containing 4.97 nmol of 3-methoxy-4-acetoxyphenylacetic acid and magnesium sulfate. To this stirring mixture is added small portions of silver trifluoroacetate until the color changes to pale yellow; the reaction mixture is stirred for an additional 1 hour.

EXAMPLE 1

9,13,14-Orthophenylacetylresiniferonyl-20-(3-acetoxy-4-methoxy-6-Iodophenylacetate) (Compound 1)

To a round bottom flask (10 mL) the following reagents were added: dichloromethane (4 mL), resiniferonol-9,13,14-orthophenylacetate (10 mg, 0.02 mmol), 4-dimethylaminopyridine (0.28 mg, 0.0022 mmol), dicyclohexylcarbodiimide (4.8 mg, 0.023 mmol), 2-Iodo-4-acetoxy-5-methoxyphenylacetic acid prepared in Procedure 1 (8.2 mg, 0.023 mmol). The reaction was stirred at room temperature, under argon, and in the dark for 24 hours. The solvent was removed in vacuo and the residue chromatographed on silica gel (chloroform). Solvent was stripped off the appropriate fractions to yield Compound 1 as a white solid (yield=10 mg; 59%). Analytical reverse phase HPLC (gradient 60–90% MeCN, 0.1% aqueous TFA) $t_R$=4.27 min, ~95%; $^1$H NMR (CDCl$_3$, 500 MHz) δ 7.44 (s, 1H), 7.35 (s,1H), 7.29 (d, 2H, J=6.8), 7.22–7.15 (m, 2H), 6.84 (s, 1H), 5.80 (s, 1H), 4.63 (s, 2H), 4.51 (s, 2H), 4.15 (d, 2H, J=2.1), 3.79–3.66 (m, 6H), 3.13 (s, 2H), 2.99 (d, 2H, J=14.3), 2.51 (t, 1H, J=7.6), 2.39 (s, 1H), 2.26 (s, 1H), 2.22 (s, 3H), 2.09–1.96 (m, 3H), 1.74 (s, 1H), 1.43 (s, 1H), 0.88 (d, 4H, J=7); $^{13}$C NMR (CDCl$_3$, 500 MHz) δ 208.2, 169.7, 168.9, 157.8, 151.4, 146.3, 139.0, 136.5, 136.3, 134.9, 134.0, 133.0, 130.8, 128.6, 127.6, 126.5, 117.7, 114.2, 110.7, 87.9, 84.4, 81.0, 80.5, 73.1, 71.3, 56.0, 55.2, 46.3, 40.9, 39.9, 39.0, 35.6, 33.9, 32.9, 24.9, 20.6, 19.9, 18.8, 10.3. Accurate mass (FAB MH+): calcd for $C_{39}H_{41}I_1O_{10}$, 797.1951; found, 797.1822.

EXAMPLE 2

9,13,14-Orthophenylacetylresiniferonyl-20-(3-hydroxy-4-methoxy-6-iodophenylacetate) (Compound 2)

9,13,14-Orthophenylacetylresiniferonyl-20-(3-acetoxy-4-methoxy-6-iodophenylacetate) (17 mg, 0.02 mmol) was dissolved in dichloromethane (1 mL) and stirred at room temperature under argon. Pyrrolidine (59.7 uL, 0.71 mmol) was then added and the reaction stirred for 2 hours after which time no starting material was visible by TLC. The solvent was removed in vacuo and the residue was purified on a TLC preparative plate (silica gel, CHCl$_3$). The product was extracted (chloroform) from the silica and the solvent evaporated after filtration to give Compound 2 as a white solid (yield=11 mg; 68%). Analytical reverse phase HPLC (gradient 40–90% MeCN, 0.1% aqueous TFA) $t_R$=4.83 min, ~90%; IR (KBr) 2850, 1732, 1705, 1504, 1270, 1027 cm$^{-1}$; $^1$H NMR (CDCl$_3$, 500 MHz) δ 7.37 (t, 1H, J=1.9), 7.31 (d, 2H, J=1.5), 7.23–7.15 (m, 1H), 6.76 (d, 1H, J=8.0), 6.72–6.67 (m, 2H), 5.80 (s, 1H), 5.48 (s, 1H), 4.63 (s, 2H), 4.59 (q, 2H, J=12.1), 4.12 (d, 1H, J=2.7), 3.8 (s, 3H), 3.49 (s, 2H), 3.14 (s, 2H), 3.0 (d, 2H, J=13.4), 2.47 (t, 1H, J=7.5), 2.35 (d, 1H, 18.9), 2.09–1.99 (m, 3H), 7.5 (s, 3H), 1.61–1.59 (s, 1 H broad), 1.44 (s, 3H), 0.88 (d, 4H, J=7.1); $^{13}$C NMR (CDCl$_3$, 500 MHz) δ 208.4, 171.4, 158.2, 146.5, 146.2, 136.5, 134.9, 134.0, 130.8, 128.5, 127.7, 126.5, 125.6, 122.2, 117.7, 114.3, 111.7, 110.7, 84.4, 81.0, 80.5, 73.3, 70.5, 65.8, 55.9, 55.3, 41.0, 40.9, 39.9, 39.0, 35.6, 33.0, 19.8, 18.8, 10.3. Accurate mass (FAB MH+): calcd for $C_{37}H_{39}I_1O_9$, 755.1741; found, 755.1717.

BIOLOGICAL EXAMPLES

Iodinated RTX derivatives of the present invention were tested for their ability to inhibit the binding of [$^3$H] RTX to hVR1 receptors in a [$^3$H] RTX Binding Assay.

Membrane preparation

HEK293 cells were transfected with human VRI vanilloid receptors, as described in U.S. patent application Ser. No. 09/292700 to Dubin, A., et. al, filed on Apr. 15, 1999 (herein incorporated by reference), and washed with Hank's Balanced Salt Solution, dissociated with cell dissocation buffer (Sigma), and then centrifuged at 1000 x g for 5 min. Cell pellets were homogenized in cold 20 mM HEPES buffer, pH 7.4, containing 5.8 mM NaCl, 320 mM sucrose, 2 mM MgCl$_2$, 0.75 CaCl$_2$ and 5 mM KCl and centrifuged at 1000 x g for 15 min. The resultant supernate was then centrifuged at 40,000 x g for 15 min. The pelleted membranes were kept in an −80° C. freezer.

The assay procedure was modified from that described in Szallasi, A. and Blumberg, P. M., "[$^3$H] Resiniferatoxin binding by the vanilloid receptor: specific-related differences, effect of temperature and sulfhydryl reagents" (Naunyn-Schmiedeberg's Arch. Pharmacol., 1993, 347, 84–91). Briefly, about 120 μg protein/ml from membranes were incubated with indicated concentrations of [$^3$H] RTX in 0.5 ml of the HEPES buffer (pH 7.4) containing 0.25 mg/mL fat acid-free bovine serum albumin at 37° C. for 60 min. The reaction mixture was then cooled to 4° C., added 0.1 mg α$_1$-acid glycoprotein to each sample and incubated at 4° C. for 15 min. The samples were centrifuged at 18500 x g for 15 min. The tip of the microcentrifuge tube containing the pellet was cut off. Bound radioactivity was quantified by scintillation counting. Non-specific binding was tested in the presence of 200 nM unlabeled RTX.

Membrane Incubation with [$^3$H] RTX and Iodinated RTX Derivatives

Membranes were incubated with [$^3$H] RTX (0.4 nM) and varying concentrations of iodinated RTX derivatives at 37° C. for 60 min. As shown in Table 1, the data are representative of two experiments with each point assayed in duplicate. The results showed that the iodinated vanilloid analogs used in this study dose-dependently inhibited [$^3$H] RTX binding.

Results of Iodinated RTX Derivative Binding to hVR1 Receptors

As shown in Table 1, Compound 1 and Compound 2 demonstrated 3 to 4 times greater affinity for binding to hVR1 receptors than a RTX derivative.

TABLE 1

| IC$_{50}$ Value for Binding to a hVR1 Receptor (nM) | |
| --- | --- |
| Compound | IC$_{50}$ (nM) |
| RTX | 0.09 ± 0.12 |
| 1 | 0.31 ± 0.06 |
| 2 | 0.22 ± 0.03 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for preparing a labeled resiniferatoxin derivative compound of Formula (V):

Formula (V)